United States Patent
Forsell

(10) Patent No.: US 7,207,936 B2
(45) Date of Patent: Apr. 24, 2007

(54) CAREFUL IMPOTENCE TREATMENT APPARATUS

(75) Inventor: Peter Forsell, Zug (CH)

(73) Assignee: Potencia Medical AG, Baar (CH)

( * ) Notice: Subject to any disclaimer, the term of this patent is extended or adjusted under 35 U.S.C. 154(b) by 0 days.

(21) Appl. No.: 10/543,681

(22) PCT Filed: Jan. 31, 2003

(86) PCT No.: PCT/SE03/00172

§ 371 (c)(1),
(2), (4) Date: Jul. 28, 2005

(87) PCT Pub. No.: WO2004/066880

PCT Pub. Date: Aug. 12, 2004

(65) Prior Publication Data

US 2006/0149125 A1    Jul. 6, 2006

(51) Int. Cl.
*A61F 5/00* (2006.01)
(52) U.S. Cl. ........................................... 600/38
(58) Field of Classification Search ............ 600/38–41, 600/29–31; 128/897–899, DIG. 25; 606/151–158, 606/201–203
See application file for complete search history.

(56) References Cited

U.S. PATENT DOCUMENTS 4,756,949 A     7/1988   Spence et al.
4,982,731 A     1/1991   Lue et al.

FOREIGN PATENT DOCUMENTS

| WO | 00/15158 | 3/2000 |
| WO | 01/47434 | 7/2001 |
| WO | 01/47435 | 7/2001 |

OTHER PUBLICATIONS

International Search Report for PCT/SE03/00172 dated Aug. 22, 2003.

*Primary Examiner*—John P. Lacyk
(74) *Attorney, Agent, or Firm*—Nixon & Vanderhye P.C.

(57) ABSTRACT

A male sexual impotence treatment apparatus includes an elongate adjustable constriction member extending in a loop around a male patient's penile tissue or the prolongation thereof. An adjustment device adjusts the longitudinal extension of the constriction member in the loop to temporarily constrict the penile tissue or the prolongation thereof to restrict the penile exit blood flow to achieve erection. A layer of a soft viscoelastic material is applied on the constriction member such that it is located between the constriction member and the patient's penile tissue or the prolongation thereof at least along a portion of the constriction member to protect the penile tissue or the prolongation thereof from being eroded by the constriction member. The layer has an inwardly directed radial extension in the loop such that, when the adjustment device is operated to decrease the longitudinal extension of the constriction member in the loop, the soft layer is forced to expand radially inwardly in the loop causing a corresponding increased constriction of the penile tissue or the prolongation thereof.

14 Claims, 2 Drawing Sheets

CAREFUL IMPOTENCE TREATMENT APPARATUS

This application is the US national phase of International Application No. PCT/SE2003/000172 filed 31 Jan. 2003, which designated the U.S., the entire content of which is incorporated herein by reference.

BACKGROUND OF THE INVENTION

1. Field of the Invention

The present invention relates to a male sexual impotence treatment apparatus, comprising a constriction device implantable in a male patient, who suffers from sexual impotence, for engaging the patient's penile tissue or the prolongation thereof, the constriction device including an elongate adjustable constriction member adapted to extend in a loop around the penile tissue or the prolongation thereof, and an implantable adjustment device adapted to adjust the longitudinal extension of the constriction member in the loop to temporarily constrict the penile tissue or the prolongation thereof to restrict the penile exit blood flow to achieve erection.

The expression "penile tissue or the prolongation thereof" should be understood to mean the penile tissue extended inside the human body and following the pathway of the blood flow leaving the penis i.e. one or more exit veins from the penis, the corpus cavernosum, crura or the prolongation thereof.

2. Description of Related Art

Male sexual impotence is a widespread problem. Many different solutions to this problem have been tried. A main solution currently practised and disclosed in for instance U.S. Pat. Nos. 5,437,605 and 4,841,461 is to implant a hydraulic inflatable silicone prosthesis in the cavities of the corpora cavernosa of the patient's penis. In fluid connection with this prosthesis is a reservoir implanted in the scrotum. By manual pumping action the prosthesis is filled with fluid from the reservoir to effect erect penile condition or is emptied of fluid, which returns to the reservoir, to effect flaccid penile condition. However, there are several more or less severe disadvantages of this main solution. Above all, the penis is more or less damaged by the operation and it is practically impossible to reverse the operation. Another disadvantage is that rather strong forces act against this implanted prosthesis resulting in a significant risk of the prosthesis being broken.

Another solution to achieve erection is to restrict the blood flow leaving the penis. For example, U.S. Pat. No. 4,829,990 discloses two hydraulically operated inflatable cuffs wrapped around the respective crura. A disadvantage of such a solution is that it involves complicated surgery. Another example on this solution is given by U.S. Pat. No. 4,828,544, which discloses an artificial fistula system surgically implanted and providing a primary fistula between the femoral artery and the femoral vein and a secondary fistula for leading blood from the primary fistula to the penis. An inflatable balloon engages the primary fistula between the secondary fistula and the vein. The balloon is in fluid connection with a manually compressible reservoir implanted in the scrotum. Again, implantation of this artifical fistula system requires delicate surgery.

Yet another example on the blood flow restriction solution is given by WO 01/54626, which discloses an elongate hydraulically adjustable constriction member adapted to temporarily constrict the corpora cavernosa or crura or the prolongations thereof of a patient's penile tissue to restrict the blood flow leaving the penis to achieve erection. There are an adjustment device that includes an inflatable cavity in the elongate constriction member and hydraulic means for adding hydraulic fluid to and withdrawing hydraulic fluid from the inflatable cavity. In practice, the elongate constriction member is made of silicone, which is a material approved for implantation, and the hydraulic fluid is a liquid such as an isotonic salt liquid mixed with other conventional materials. Although this blood flow restriction solution is quite promising, it has the following disadvantage. Since the salt solution is an incompressible liquid the pressure will be the same in the entire cavity of the constriction member. In consequence, the entire constriction member will press relatively hard against the corpora cavernosa or crura or the prolongations thereof when the hydraulic fluid is added to the constriction member, which over time might be injurious to the corpora cavernosa or crura or the prolongations thereof.

SUMMARY OF THE INVENTION

The object of the present invention is to provide a new convenient adjustable impotence treatment apparatus designed to carefully constrict the penile tissue or the prolongation thereof of an impotent patient to restrict the penile exit blood flow to achieve erection.

This object is achieved by an apparatus of the kind described initially characterised by a layer of a soft viscoelastic material, which is applied on the constriction device such that it is located between the constriction device and the patient's penile tissue or the prolongation thereof at least along a portion of the constriction member, when the constriction device is implanted, to protect the penile tissue or the prolongation thereof from being eroded by the constriction device, and in that the layer of viscoelastic material has an inwardly directed radial extension in the loop such that when the adjustment device is operated to decrease the longitudinal extension of the constriction member, the layer of viscoelastic material is forced to expand radially inwardly in the loop causing a corresponding increased constriction of the penile tissue or the prolongation thereof.

The constriction device may be implanted in the base of the patient's penis or the prolongation thereof and preferably may engage the corpus cavernosum, crura or the prolongation thereof of the penis. However, there are several alternative positions of the constriction device that give more or less satisfactory restriction of the blood flow leaving the penis. Thus, as a first alternative the constriction device may extend around both corpora cavernosa or crura of the penis as a single unit. As a second alternative the constriction device may comprise two elongated constriction members extending around the respective corpora cavernosa or crura. As a third alternative an elongated constriction member of the constriction device may encircle one or more of the penile exit veins. As a fourth alternative the constriction device may comprise several constriction members extending around the respective penile exit veins.

This results in the important advantage that it is not the constriction member, usually made of a relatively hard silicone material, itself that directly abuts and presses against the penile tissue or the prolongation thereof. Rather, it is the layer of viscoelastic material that carefully abuts and presses against the penile tissue or the prolongation thereof as it is expanded inwardly in the loop.

Another important advantage achieved by the present invention is that, depending on the thickness of the layer of viscoelastic material, a relatively small change in the longitudinal extension of the constriction member made by the adjustment device may result in a relatively large change in the restriction of the blood flow leaving the patient's penis.

For example, the viscoelastic material may comprise a foam or gel of polymer.

Advantageously, the layer of viscoelastic material may completely cover the elongate constriction member and be divided into a series of separate elongate cells of viscoelastic material distributed around the elongate constriction member. As a result, the viscoelastic material located on the inner side of the loop formed by the elongate constriction member is prevented from flowing to the outer side of said loop when the constriction device is adjusted to constrict the penile tissue or the prolongation thereof.

Generally, the adjustment device comprises a powered adjustment device, for example including a motor, preferably an electric motor. The apparatus may comprise an implantable energy-transforming device adapted to transform wireless energy emitted from outside the patient's body into an energy form suited for powering the adjustment device. Such an energy form may be electric energy for powering an electric motor of the adjustment device.

To conveniently adjust the constriction device the apparatus may comprise a wireless remote control for controlling the adjustment device from outside the patient's body.

In accordance with an embodiment of the invention the constriction member comprises a hydraulic constriction member, typically with an inflatable cavity, and the adjustment device comprises a pump hydraulically connected to the hydraulic constriction device.

In a preferred simple mechanical embodiment of the invention, the constriction member is non-inflatable and comprises a main portion and two elongated end portions. The adjustment device is adapted to establish longitudinal relative displacement between the end portions of the constriction member, such that the constriction of the penile tissue or the prolongation thereof is adjusted. Since a relatively small change in the longitudinal extension of the constriction member may result in a relatively large change in the restriction of the blood flow leaving the penis, the adjustment device may be designed very simple, because the necessary stroke of the displacement between the end portions of the constriction member can be very short.

The adjustment device suitably comprises a movement-transferring member in engagement with at least one of the end portions of the constriction member and operable to displace said one end portion relative to the other end portion of the constriction member. The movement-transferring member may comprise a gear wheel fixed to the other end portion of the constriction member and a gear rack formed on the one end portion of the constriction member, the gear wheel and the gear rack being in mesh with each other. A motor may be connected to the gear wheel and a worm gear may be connected between the motor and the gear wheel. The motor, worm gear, gear wheel and gear rack are suitably contained in a rigid housing that may be at least in part covered with the layer of soft viscoelastic material to protect the penile tissue or the prolongation thereof.

DETAILED DESCRIPTION OF THE INVENTION

Figure 1:
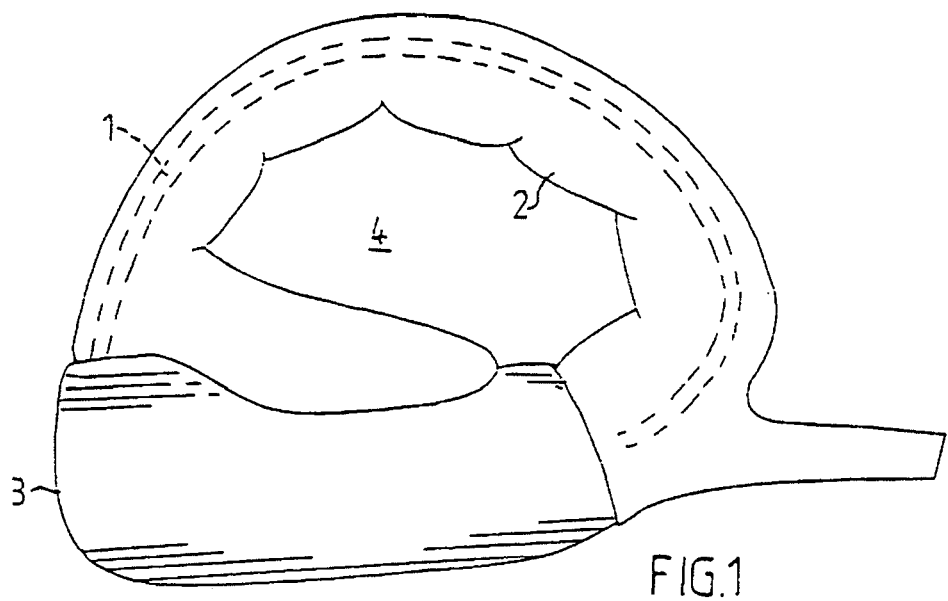
FIG. 1 is a view of an apparatus according to an embodiment of the present invention having a mechanical constriction member in a non-constricted state.
Figure 2:
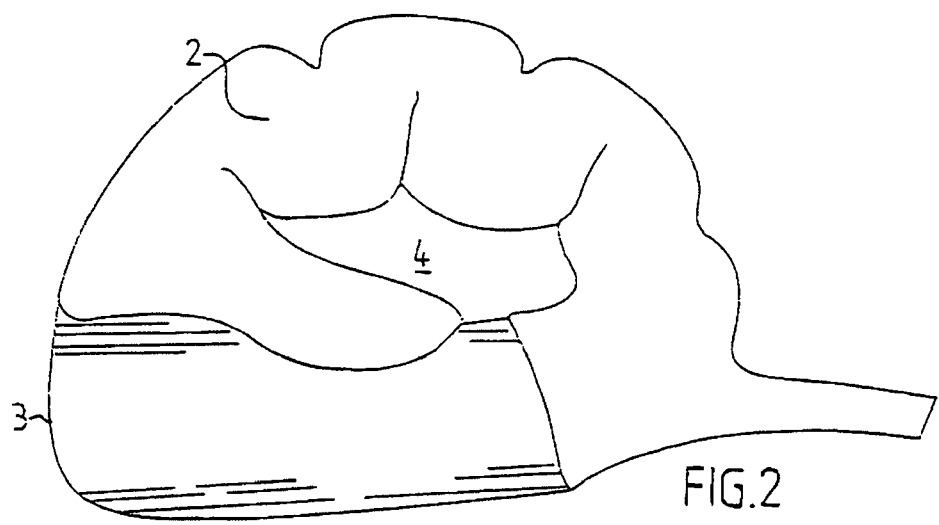
FIG. 2 is a view of the apparatus of FIG. 1 with the constriction member in a constricted state.

FIG. 1 shows a constriction device of an apparatus of the present invention including an elongated constriction member in the form of a flexible plastic band 1 and a protective layer 2 of a viscoelastic material, such as silicone having hardness less than 20 Shore, applied on the band 1, so that the band 1 is embedded in the protective layer 2. Two end portions of the band 1 are connected to an elongate housing 3 containing an adjustment device, which is capable of establishing longitudinal relative displacement between the end portions. The band 1 and the housing 3 form a closed loop defining a restriction opening 4. FIG. 1 illustrates the apparatus when the restriction opening 4 is relatively large, whereas FIG. 2 illustrates the apparatus when the adjustment device has been operated to pull the end portions together causing the viscoelastic material of the layer 2 to expand inwardly in the loop, so that the restriction opening 4 is reduced. When the constriction device is implanted in an impotent patient, for example with the band 1 applied around the patient's penile tissue 18 as illustrated in FIG. 4, the restriction of the penile exit blood flow is correlated to the size of the restriction opening 4.

Figure 3:
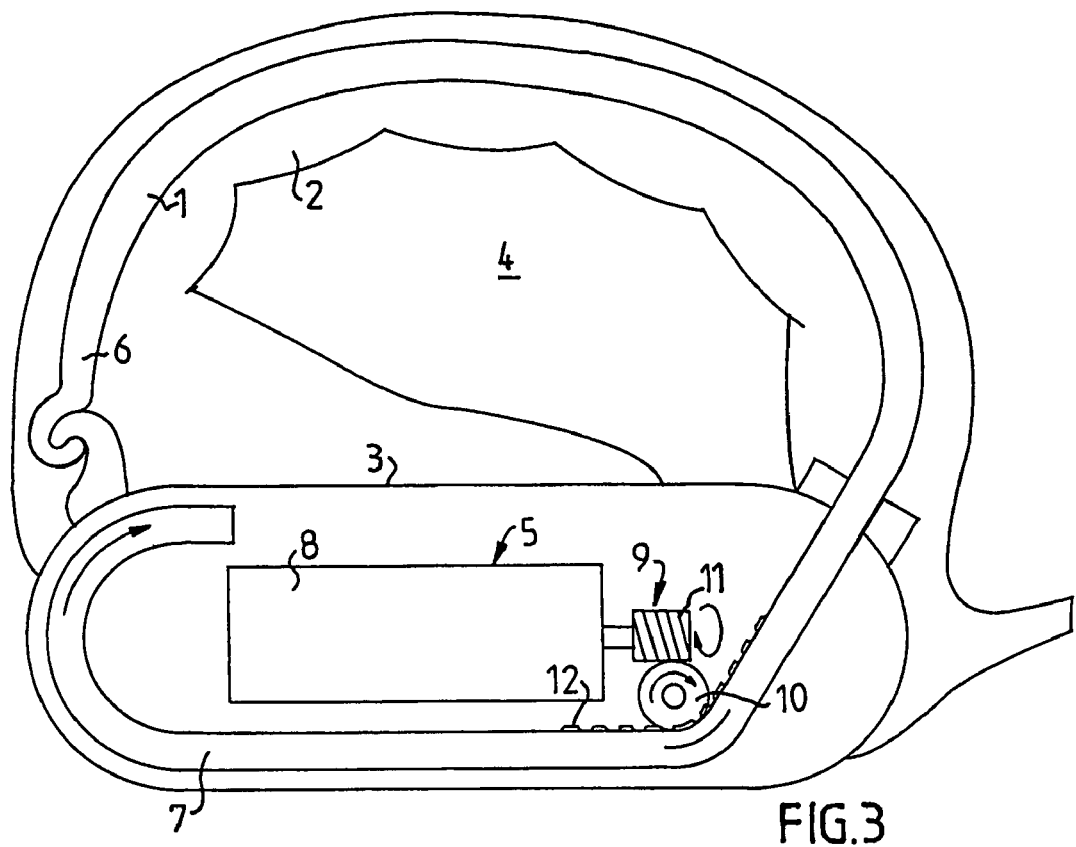
FIG. 3 is a schematic sectional view of the embodiment shown in FIG. 1.

With reference to FIG. 3, the adjustment device 5 will be described in more detail. The band 1 has a first end portion 6 releasably connected to the housing 3 and a second end portion 7 connected to the adjustment device 5. The adjustment device 5 includes an electric motor 8 and a movement transferring means 9 in engagement with the end portion 7. The electric motor 8 operates the movement transferring means 9 to displace the end portion 7 relative to portion 6 in the loop formed by the band 1 and housing 3. The movement-transferring means 9 includes a gear wheel 10 fixed to the housing 3, a worm gear 11 connected between the electric motor 8 and the gear wheel 10, and a gear rack 12 formed on the end portion 7, wherein the gear wheel 10 and the gear rack 12 are in mesh with each other.

Figure 4:
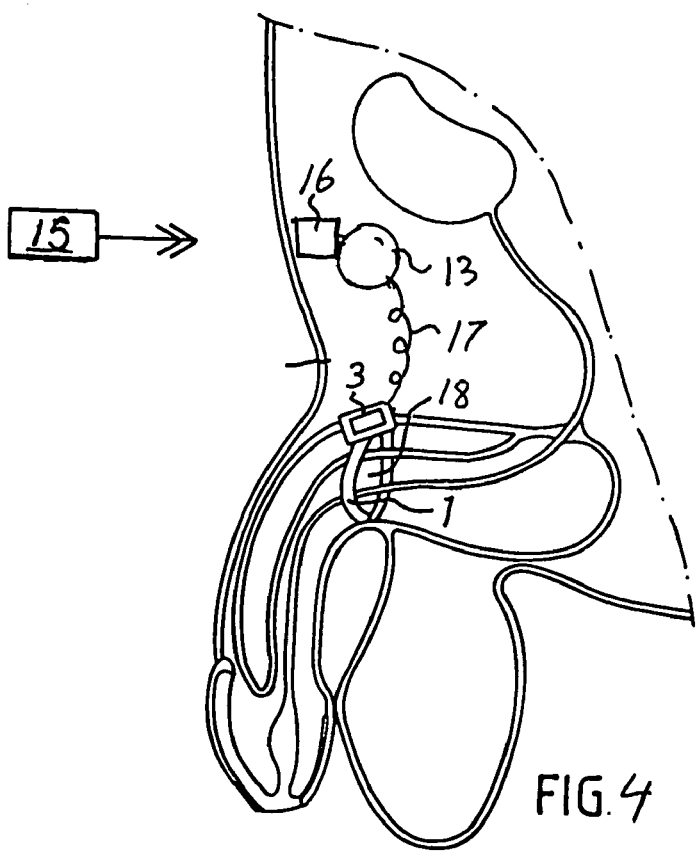
FIG. 4 illustrates the apparatus according to FIGS. 1 and 2 implanted in an impotent patient.

FIG. 4 illustrates the constriction device of the embodiment shown in FIGS. 1 and 2 applied on the penile tissue 18 of an impotent patient. The band 1 and housing 3 of the constriction device extend in a loop around the penile tissue. A rechargeable electric power supply 13 is implanted in the patient. An external remote control 15 controls the adjustment device 5 and transmits signals that are received by a combined control and energy-transforming unit 16 subcutaneously implanted in the patient. The unit 16 is electrically connected to the electric power supply 13 and transforms the energy of the signals into an electric current that is used for charging the electric power supply 13. For example, the signals may include electromagnetic waves and the unit 16 may include an electric p-n junction element that transforms the wireless energy into an electric current. A resilient insulated electric wire 17 connects the power supply 13 and the electric motor 8 in the housing 3. The electric wire 17 extends helically between the power supply 13 and housing 3, in order to permit the electric wire 17 to be temporarily extended when movements of the penile tissue occur, so that the risk of breaking the electric wire 17 is eliminated.

Figure 5:
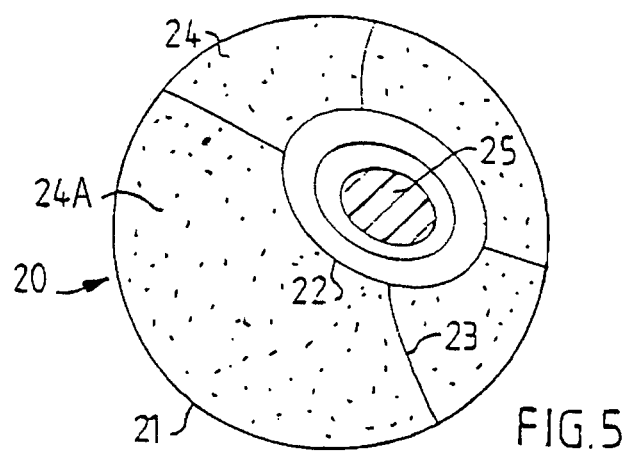
FIG. 5 is a cross-section of a mechanical constriction device according to another embodiment of the invention.

FIG. 5 shows a cross-section of a mechanical constriction device of another embodiment of the invention, comprising a double walled tubing 20, an external wall 21 and an internal wall 22 spaced from the external wall 21. The tubing 20 has partition walls 23 dividing the space between the external and internal walls 21 and 22, respectively, of the tubing 20 into longitudinal cells 24, which are filled with a soft viscoelastic material, such as a gel. A constriction member in the form of a strong band 25 of nylon or the like slides in the tubing 20 to enable adjustment of the constriction device. One cell 24A is larger than the other cells 24 and intended to abut against the penile tissue or the prolongation thereof when the band 2 extends in a loop around the penile tissue or the prolongation thereof. As a result, when the constriction device is adjusted to constrict the penile tissue or the prolongation thereof, the viscoelastic material located in cell 24A is prevented from flowing to the cells 24 that will be located more or less on the outer side of the loop that does not contact the penile tissue or the prolongation thereof.

The invention claimed is:

1. A male sexual impotence treatment apparatus, comprising a constriction device implantable in a male patient, who suffers from sexual impotence, for engaging the patient's penile tissue or the prolongation thereof, the constriction device including an elongate adjustable constriction member extending in a loop around the penile tissue or the prolongation thereof, and an implantable adjustment device for adjusting the longitudinal extension of the constriction member in the loop to temporarily constrict the penile tissue or the prolongation thereof to restrict the penile exit blood flow to achieve erection, a layer of a soft viscoelastic material being applied on the constriction device such that the layer is located between the constriction device and the patient's penile tissue or the prolongation thereof at least along a portion of the constriction member, when the constriction device is implanted, to protect the penile tissue or the prolongation thereof from being eroded by the constriction device, the layer of viscoelastic material having an inwardly directed radial extension in the loop, such that when the adjustment device is operated to decrease the longitudinal extension of the constriction member in the loop, the layer of viscoelastic material is forced to expand radially inwardly in the loop, causing a corresponding increased constriction of the penile tissue or the prolongation thereof, wherein the layer of viscoelastic material is divided into a series of separate elongate cells of viscoelastic material distributed around the elongate constriction member.

2. An apparatus according to claim 1, wherein the viscoelastic material comprises a foam or gel.

3. An apparatus according to claim 1, wherein the constriction member is non-inflatable.

4. An apparatus according to claim 3, wherein the constriction member comprises a main portion and two elongated end portions, and the adjustment device establishes longitudinal relative displacement between the end portions of the constriction member.

5. An apparatus according to claim 4, wherein the adjustment device comprises a movement transferring means in engagement with at least one of the end portions of the constriction member and operable to displace the one end portion relative to the other end portion of the constriction member.

6. An apparatus according to claim 5, wherein the movement transferring means comprises a gear wheel fixed to the other end portion of the constriction member and a gear rack formed on the one end portion of the constriction member, the gear wheel and the gear rack being in mesh with each other.

7. An apparatus according to claim 6, wherein the adjustment device comprises a motor connected to the gear wheel.

8. An apparatus according to claim 7, wherein the adjustment device comprises a worm gear connected between the motor and the gear wheel.

9. An apparatus according to claim 1 further comprising a rigid housing containing the adjustment device.

10. An apparatus according to claim 1, wherein the adjustment device comprises a motor.

11. An apparatus according to claim 1, wherein the constriction member comprises a hydraulic constriction member and the adjustment device comprises a pump hydraulically connected to the hydraulic constriction member.

12. An apparatus according to claim 1, wherein the adjustment device comprises a powered adjustment device and further comprising an implantable energy transforming device adapted to transform wireless energy emitted from outside the patients body into an energy form suited for powering the adjustment device.

13. An apparatus according to claim 1, further comprising a wireless remote control for controlling the adjustment device to adjust the constriction device.

14. An apparatus according to claim 1, wherein the layer of viscoelastic material has a thickness such that a relatively small change in the longitudinal extension of the constriction member in the loop results in a relatively large change in the blood flow leaving the patient's penis.

* * * * *